United States Patent
Chatterjee et al.

(10) Patent No.: US 6,977,242 B2
(45) Date of Patent: Dec. 20, 2005

(54) TWO GONADOTROPIN RELEASING HORMONES AND A METHOD TO ISOLATE THE SAME

(75) Inventors: Abhijit Chatterjee, West Bengal (IN); Partha Ray, West Bengal (IN); Subrata Dasgupta, West Bengal (IN); Samir Hattacharya, Kolkata (IN); Santosh Pasha, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/354,433

(22) Filed: Jan. 28, 2003

(65) Prior Publication Data

US 2003/0236185 A1 Dec. 25, 2003

Related U.S. Application Data

(60) Provisional application No. 60/353,041, filed on Jan. 30, 2002.

(51) Int. Cl.$^7$ .................. A61K 38/22; C07K 14/575
(52) U.S. Cl. .................. 514/15; 514/15; 514/8; 514/14; 514/2; 530/313; 530/327; 530/398; 930/130
(58) Field of Search .................. 514/15, 8, 14, 514/2; 530/313, 327, 398; 930/130

*Primary Examiner*—Christopher R. Tate
*Assistant Examiner*—B. Dell Chism
(74) *Attorney, Agent, or Firm*—Ladas & Parry LLP

(57) ABSTRACT

The present invention relates to two novel Gonadotropin releasing hormones muGnRH I and muGnRH II of amino acid SEQ ID 1 as QHWSAWRLPG, and SEQ ID 2 QHWSWGILPG respectively, useful for induced breeding in fish both in combination and alone, by activating production of Gonadotropin, and a method of isolating the same from Indian Murrel brain, and further, a method of inducing breeding in fishes using the said novel gonadotropin releasing hormones.

11 Claims, 8 Drawing Sheets

| GnRH | 1 2 3 4 | 5 6 7 8 | 9 10 |
|---|---|---|---|
| Mammalian | pGlu-His-Trp-Ser- | Tyr-Gly-Leu-Arg- | Pro-Gly-NH$_2$ |
| Guinea Pig | pGlu-Tyr-Trp-Ser- | Tyr-Gly-Val-Arg- | Pro-Gly-NH$_2$ |
| Chicken I | pGlu-His-Trp-Ser- | Tyr-Gly-Leu-Gln- | Pro-Gly-NH$_2$ |
| Chicken II | pGlu-His-Trp-Ser- | His-Gly-Trp-Tyr- | Pro-Gly-NH$_2$ |
| Salmon | pGlu-His-Trp-Ser- | Tyr-Gly-Trp-Leu- | Pro-Gly-NH$_2$ |
| Lamprey I | pGlu-His-Tyr-Ser- | Leu-Glu-Trp-Lys- | Pro-Gly-NH$_2$ |
| Lamprey III | pGlu-His-Trp-Ser- | His-Asp-Trp-Lys- | Pro-Gly-NH$_2$ |
| Tunicate I | pGlu-His-Trp-Ser- | Asp-Tyr-Phe-Lys- | Pro-Gly-NH$_2$ |
| Tunicate II | pGlu-His-Trp-Ser- | Leu-Cys-His-Ala- | Pro-Gly-NH$_2$ |
| Catfish | pGlu-His-Trp-Ser- | His-Gly-Leu-Asn- | Pro-Gly-NH$_2$ |
| Dogfish | pGlu-His-Trp-Ser- | His-Gly-Trp-Leu- | Pro-Gly-NH$_2$ |
| Sea Bream | pGlu-His-Trp-Ser- | Tyr-Gly-Leu-Ser- | Pro-Gly-NH$_2$ |
| Herring | pGlu-His-Trp-Ser- | His-Gly-Leu-Ser- | Pro-Gly-NH$_2$ |

FIG. 1. Comparison of primary amino acid sequences of naturally occurring vertebrates and protochordate GnRHs.

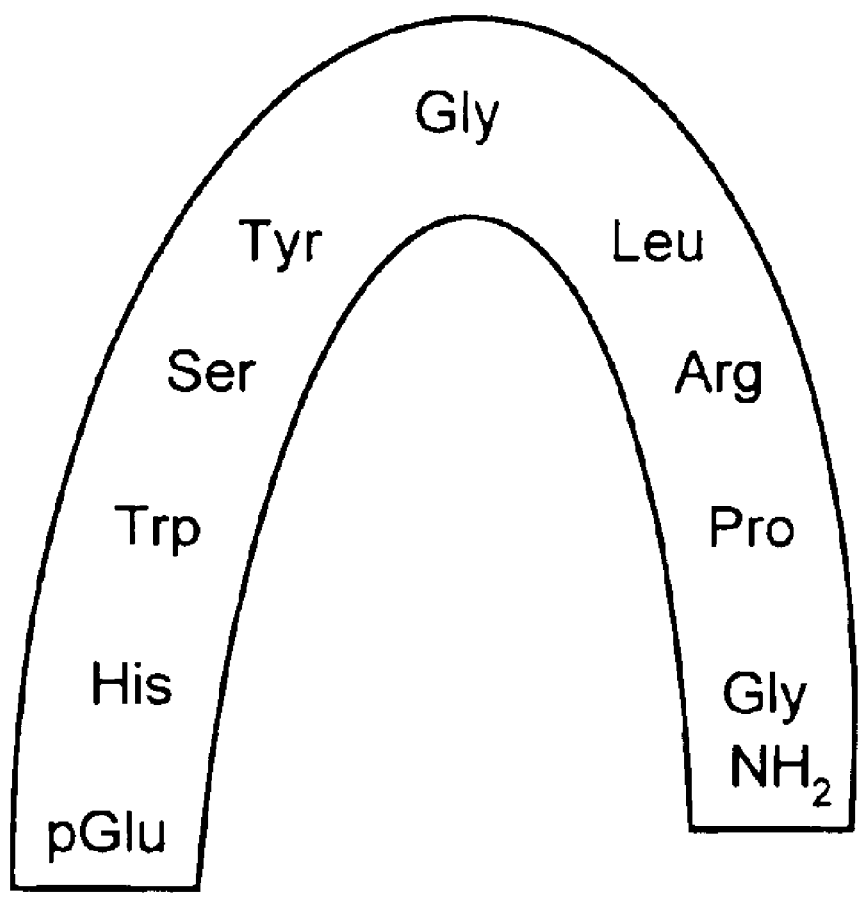
FIG. 2. Hairpin loop of GnRN

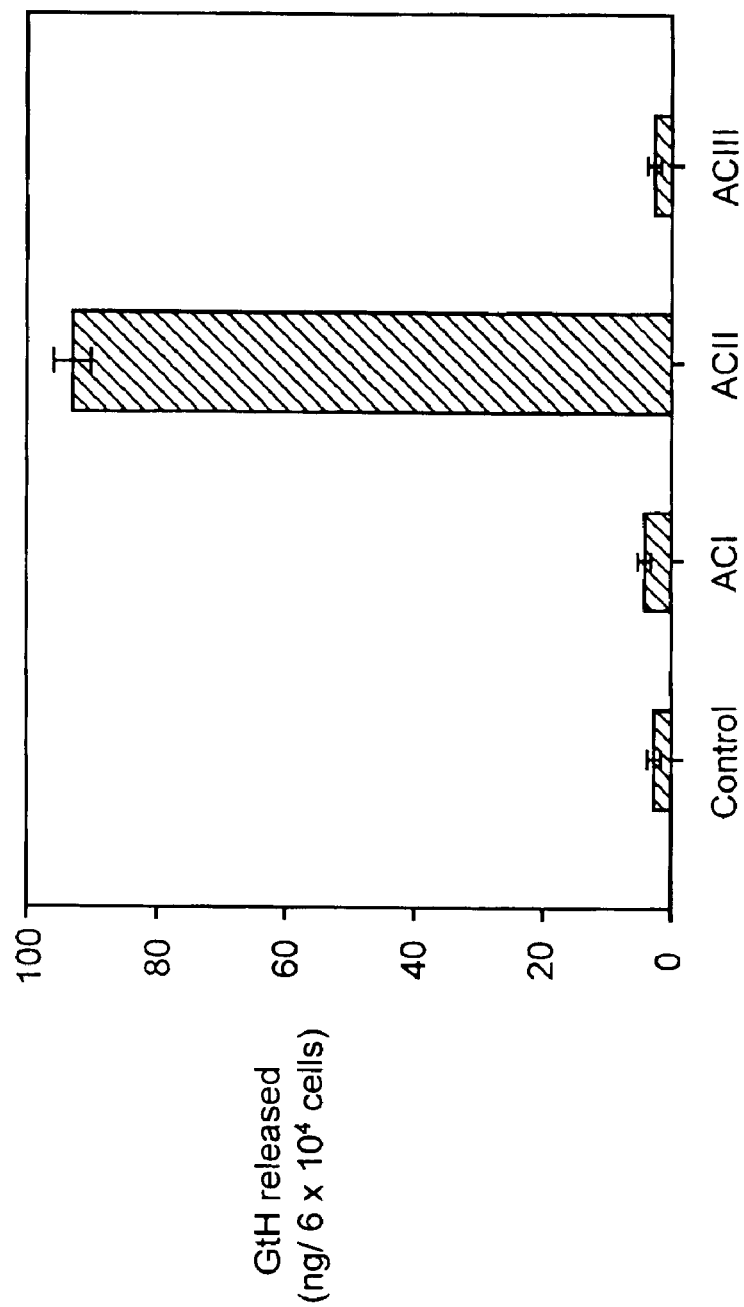
F I G. 3. Test of murrel GnRH bioactivity in different fractions obtained through acetone fractionation.

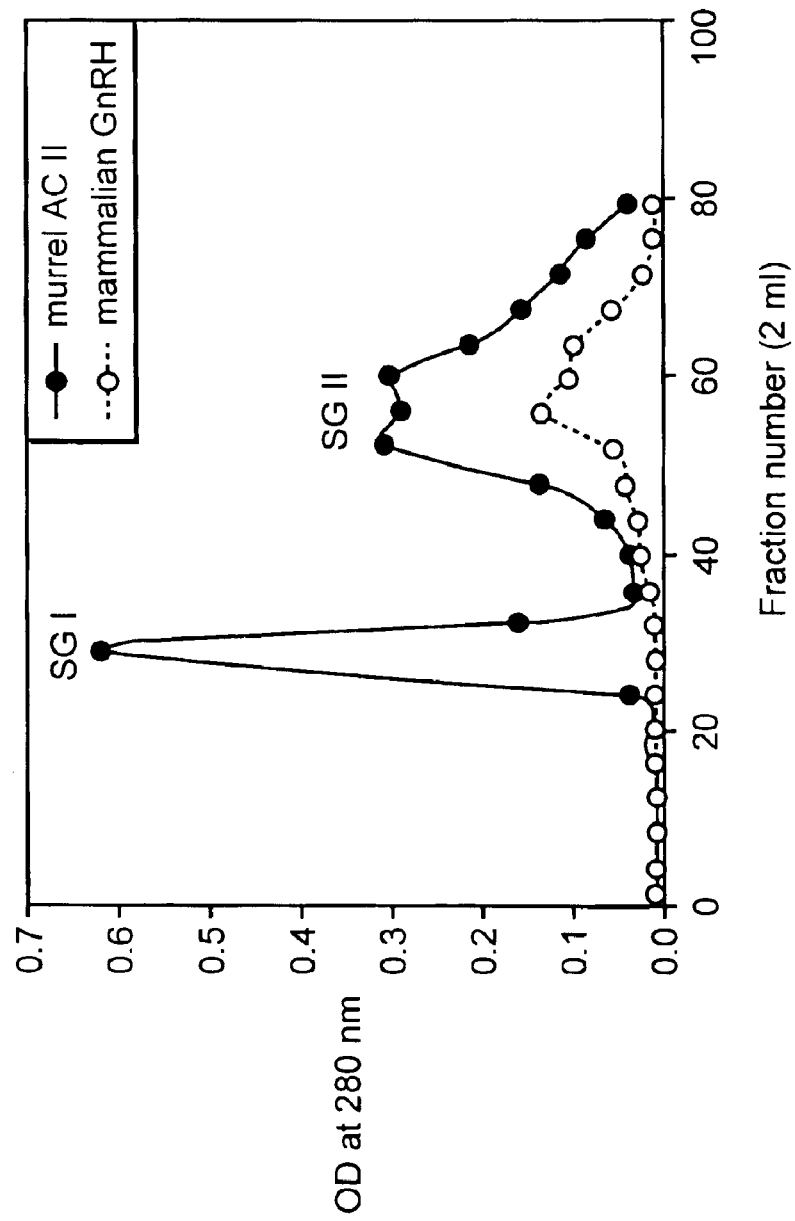
FIG. 4. Elution profile of mammalian GnRH through Sephadex G-25 column.

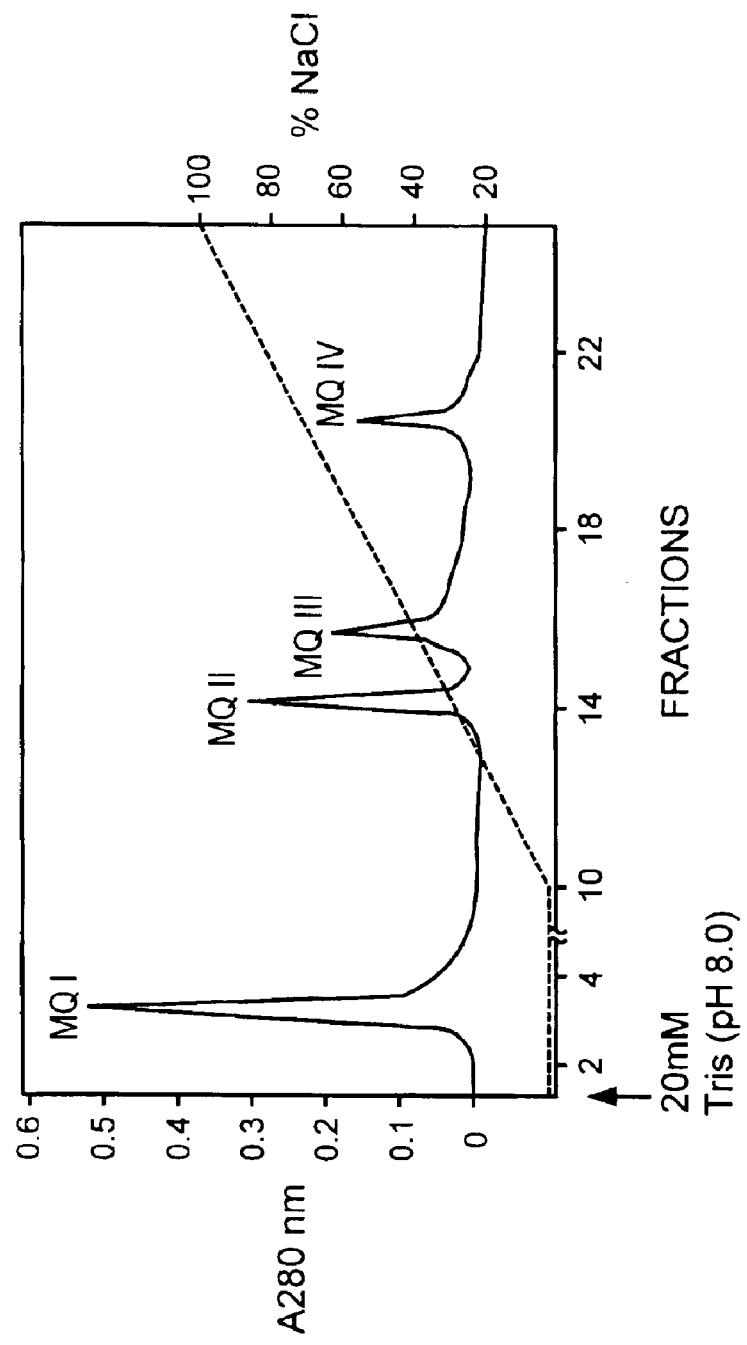
FIG. 5a. Elution profile of murrel Sephadex C-25 P-II through FPLC Mono Q column

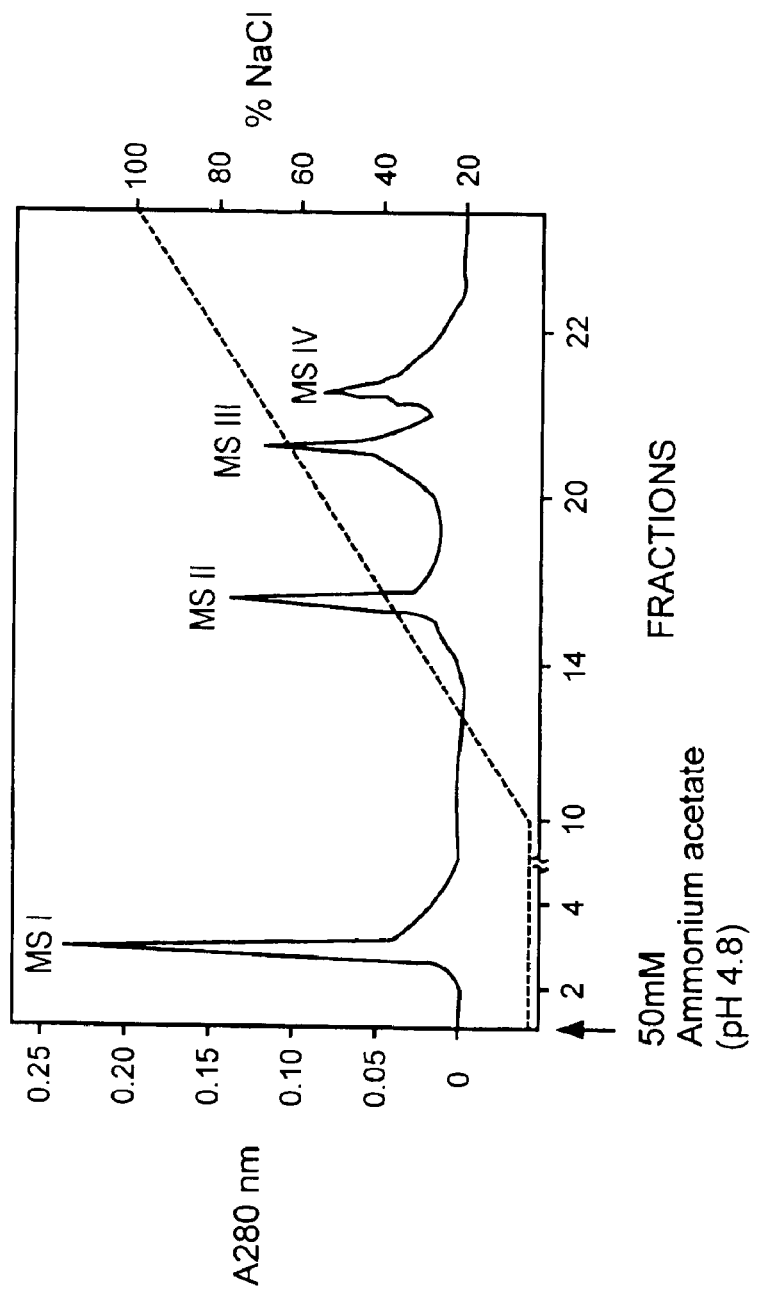
F I G. 5b. Elution profile of murrel Mono Q unbound peak (MQ I) through FPLC Mono S column.

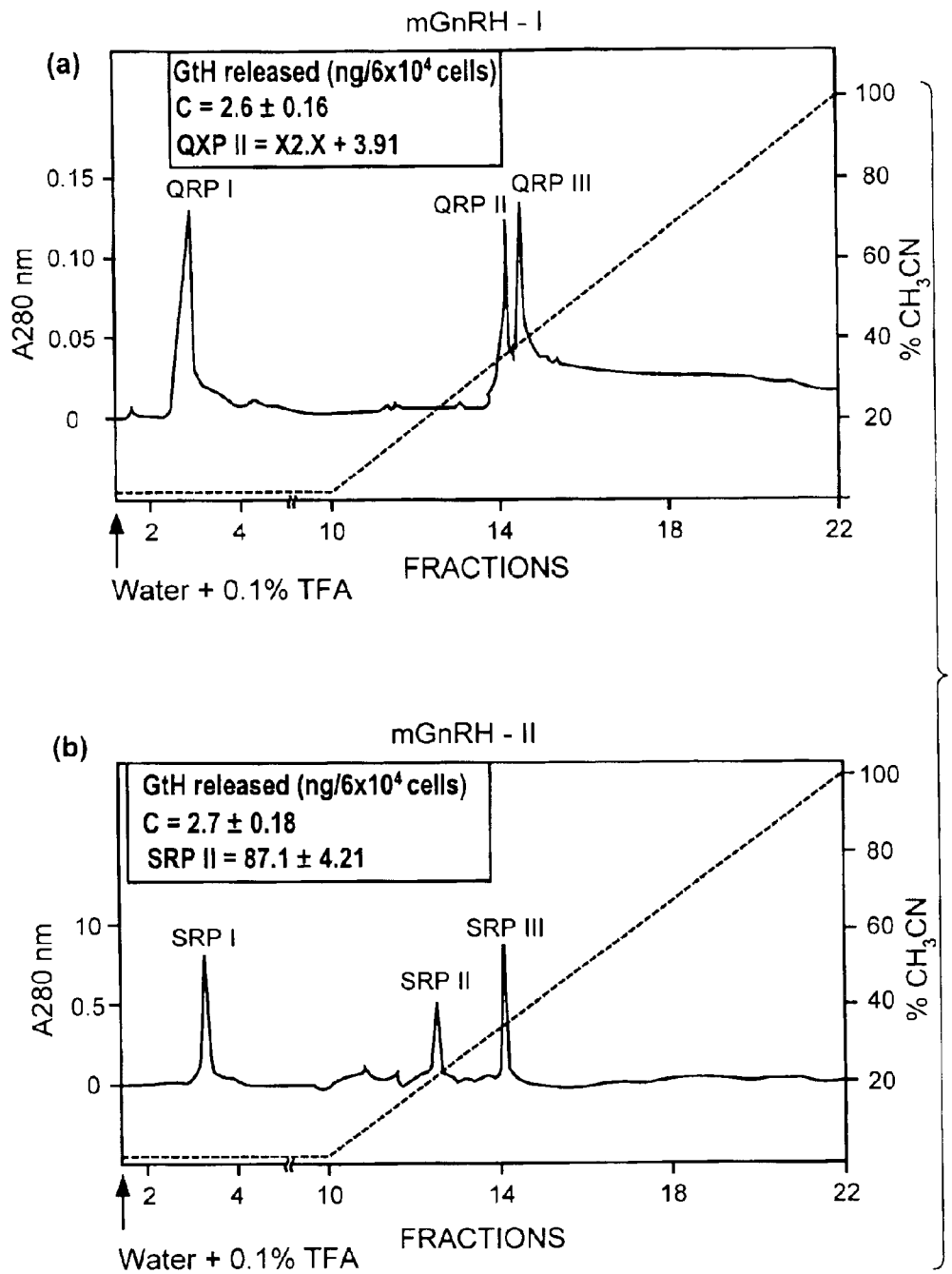
FIG. 6. Elution profile of Mono QP-II (a) and Mono SP-II (b) through FPLC Pep-RPC column.

Murrel GnRH I: pGlu-His-Trp-Ser-Ala-Tyr-Arg-Leu-Pro-Gly-NH$_2$
Murrel GnRH II: pGlu-His-Trp-Ser-Tyr-Gly-Ile-Lys/Pro-Gly-NH$_2$ FIG. 7. Amino acid sequences of murrel GnRH I and II.

TWO GONADOTROPIN RELEASING HORMONES AND A METHOD TO ISOLATE THE SAME

This application claims the benefit of U.S. Provisional Application(s) No(s).: 60/353,041 Jan. 30, 2002 and incorporates the same by reference.

FIELD OF THE PRESENT INVENTION

The present invention relates to two novel Gonadotropin releasing hormones muGnRH I and muGnRH II of amino acid SEQ ID 1 as QHWSAWRLPG, and SEQ ID 2 QHWSWGILPG respectively, useful for induced breeding in fish both in combination and alone, by activating production of Gonadotropin, and a method of isolating the same from Indian Murrel brain, and further, a method of inducing breeding in fishes using the said novel gonadotropin releasing hormones.

BACKGROUND AND PRIOR ART WORK

Gonadotropin Releasing Hormone (GnRH) is now the best available biotechnological tool for the induced breeding of fish. GnRH is the key regulator and central initiator of reproductive cascade in all vertebrates.

It's a decapeptide and first isolated from pig and sheep hypothalami with the ability to induce pituitary release of luteinising hormone (LH) and follicle stimulating hormone (FSH). Since then only one form of GnRH has been identified in most placental mammals including human beings as the sole neuropeptide causing the release of LH and FSH.

However, in non-mammalian species (except guinea pig) twelve GnRH variants have now been structurally elucidated, among them seven different forms have been isolated from fish species. Depending on the structural variants and their biological activities number of chemical analogues have been prepared and one of them is sahnon GnRH analogue profusely used now in fish breeding and marketed commercially throughout the world. Question is why fishes require an induction by this neuropeptide hormone to release germ cells from male and female partners so that fertilization of oocytes by sperms may occur in the aquatic ambience.

In fact, most of the economically important culturable fish in land-locked water do not breed until they are induced by the hormone. Fish in marine or riverine water do not need induction by hormone for their breeding. But to culture fish with the intention of increasing the yield of production in either ocean or river is not possible. Culture requires a controllable area, that's why pisciculture to enhance the yield is restricted to land-locked aquatic bodies where fish do not usually breed or spawn without the induction of hormone.

Since fish meat has been found to be the best quality food among all animal meats, there is an enormous increase in fish producing industries in global scenario recently where the major rate-limiting factor is breeding. The induced breeding of fish is now successfully achieved by the development of GnRH technology. In this overview, a brief description is given to conceive the biotechnology of this highly important area of our food supplement.

Structure of GnRH—GnRH was first isolated from the mammalian hypothalamus as a decapeptide(Burgus et al., 1972; Mastuo et al., 1971). Since then, several structural variants of GnRH have been described which can be seen in FIG. 1 (shown under the heading brief description of accompanying drawings).

There has been a striking conservation in GnRH peptide length, the first four —NH2 terminus and two —COOH terminus amino acids are remarkably conserved in different vertebrates. Whatever changes occurred are between 5 and 8 amino acid residues, position 8 is most variable followed by position 6,5 and 7. This highly variable position 8 suggests its role in the variation of biological activity between the species and its critical function in recognizing GnRH receptors on the pituitary cell membrane. To exert its biological function it has to first recognize its receptor on the pituitary gonadotroph cell membrane and when it has to do so its linear structure changes into a loop. The NH2- and COOH-terminal domain of GnRH are closely opposed when GnRH binds to its receptor and this is the proposed result from a P-II type rum involving resides 5–8. The P turn creates a hairpin loop that aligns N and C termini (Sealfon et al., 1997) (FIG. 2). (Shown under the heading brief description of accompanying drawings).

GnRH from Indian fish—Although India has several varieties of indigenous culturable bony fish, practically nothing is known about their GnRH. This is really a very unfortunate situation for which we still have to depend on the supply from other countries to investigate the reproductive biology of our economically important culturable fish as GnRH is the key regulator of reproductive control mechanism.

Several years ago we initiated this research and faced serious problems. For the isolation of this peptide we would need an assay system to identify the desired molecule at each step of purification. First piscine GnRH isolated purified and structure determined was Salmon GnRH (Sherwood and her associates in 1983), and the most current GnRH purified and characterized by two different groups Carolsfeld et al and Robinson et al., was in 2000. Between the span of this time, number of GnRH variants have been isolated by depending on the immunoreactivity of this molecule. During Salmon GnRH isolation, Sherwood et al took the help of anti-GnRH antibody from mammalian source, later they developed Salmon anti-GnRH antibody which permitted to isolate different GnRH forms from other sources.

Meanwhile Jamaluddin et al, (Gen comp Endocrinology May 1989; 74(2): 190-8) of applicants laboratory developed a very dependable GnRH bioassay. Basic principle of this bioassay is to get the release of GTH from murrel primary pituitary cell culture and determine the amount of GTH released by GTH-RIA.

OBJECTS OF THE PRESENT INVENTION

The main object of the present invention is to isolate and identify novel gonadotropin releasing hormones for induced breeding in fishes.

Another main object of the present invention is to develop a method of isolating and sequencing novel gonadotropin releasing hormones from Indian Murrel brain.

Yet another object of the present invention is to develop gonadotropin-releasing hormones for enhanced release of gonadotropin in fishes.

Still another object of the present invention is to develop gonadotropin-releasing hormones showing synergistic effect.

Still another object of the present invention is to develop various fractions of hypothalami with gonadotropin releasing hormone activity.

Still another object of the present invention is to determine the effect of calcium on the gonadotropin hormone releasing activity of GnRH.

Still another embodiment of the present invention is to develop a method of inducing breeding in fishes using the said novel gonadotropin releasing hormones.

SUMMARY OF THE PRESENT INVENTION

The present invention relates to two novel Gonadotropin releasing hormones muGnRH I and muGnRH II of amino acid SEQ ID 1 as QHWSAWRLPG, and SEQ ID 2 QHWSWGILPG respectively, useful for induced breeding in fish both in combination and alone, by activating production of Gonadotropin, and a method of isolating the same from Indian Murrel brain, and further, a method of inducing breeding in fishes using the said novel gonadotropin releasing hormones.

DETAILED DESCRIPTION OF THE PRESENT INVENTION

Accordingly, the present invention relates to two novel Gonadotropin releasing hormones muGnRH I and muGnRH II of amino acid SEQ ID 1 as QHWSAWRLPG, and SEQ ID 2 QHWSWGILPG respectively, useful for induced breeding in fish both in combination and alone, by activating production of Gonadotropin, and a method of isolating the same from Indian Murrel brain, and further, a method of inducing breeding in fishes using the said novel gonadotropin releasing hormones.

Further, the present invention relates to two novel Gonadotropin releasing hormones muGnRH I and muGnRH II of amino acid sequence QHWSAWRLPG and QHWSWGILPG respectively, useful for induced breeding in fishes both in combination and alone, by activating production of Gonadotropin.

In an embodiment of the present invention, said hormones are obtained from Indian Murrel brain.

In another embodiment of the present invention, muGnRH II is a more active gonadotropin releasing hormone than muGnRH I.

In yet another embodiment of the present invention, muGnRH I increase gonadotropin release by about 30 times.

In still another embodiment of the present invention, muGnRH II increase gonadotropin release by about 35 times.

In still another embodiment of the present invention, wherein both muGnRH I, and muGnRH II in combination in the ratio of about 1:1 increase gonadotropin release by about 50 times.

In still another embodiment of the present invention, said hormones show synergy in induced breeding of fishes.

In still another embodiment of the present invention, both muGnRH I and muGnRH II in combination increase gonadotropin release by about 50 times.

In still another embodiment of the present invention, said hormones show no species barrier in induced breeding of fishes with increase in gonadotropin release ranging between 20–50 times.

In still another embodiment of the present invention, said hormones are more active than other GnRHs comprising mammalian GnRH, Salmon GnRH, GnRH superactive analogues, and commercially available GnRH Ovaprim, both in combination and alone.

In an embodiment of the present invention, a method of isolating and sequencing two novel Gonadotropin releasing hormones muGnRH I and muGnRH II of amino acid sequence QHWSAWRLPG and QHWSWGILPG respectively, useful for induced breeding in fishes both in combination and alone, by activating production of Gonadotropin.

In another embodiment of the present invention, homogenizing hypothalami in acidic conditions.

In yet another embodiment of the present invention, filtering said homogenate to remove fat and cell debris.

In still another embodiment of the present invention, adding acetone in a stepwise manner to the said filtrate to obtain three precipitates namely AC I, AC II, and AC III.

In still another embodiment of the present invention, estimating Gonadotropin Releasing Hormone (GnRH) activity in the said precipitates.

In still another embodiment of the present invention, fractionating only active precipitate AC II further using Molecular Exclusion Chromatography to obtain fractions SG I and SG II.

In still another embodiment of the present invention, estimating Gonadotropin Releasing Hormone (GnRH) activity in the fractions of previous step.

In still another embodiment of the present invention, fractionating only active fraction SG II further, using Ion Exchange Chromatography with anionic column to collect fractions MQ I, MQ II, MQ III, and MQ IV.

In still another embodiment of the present invention, estimating Gonadotropin Releasing Hormone (GnRH) activity in the fractions of previous step, with only fractions MQ I and MQ II having the same.

In still another embodiment of the present invention, fractionating MQ I further, using Ion Exchange Chromatography with cationic column to obtain fractions MS I, MS II, MS III, and MS IV.

In still another embodiment of the present invention, estimating Gonadotropin Releasing Hormone (GnRH) activity in the fractions of previous step with only fraction MS II having the same.

In still another embodiment of the present invention, fractionating MS II fraction using Reverse Phase Chromatography to obtain fractions SRP I, SRP II, and SRP III.

In still another embodiment of the present invention, estimating Gonadotropin Releasing Hormone (GnRH) activity in the fractions of previous step with only fraction SRP II having the same.

In still another embodiment of the present invention, fractionating MQ II further, using Reverse Phase Chromatography to obtain fractions QRP I, QRP II, and QRP III.

In still another embodiment of the present invention, calculating Gonadotropin Releasing Hormone (GnRH) activity in the fractions of previous step with only fraction QRP II having the same.

In still another embodiment of the present invention, sequencing QRP II and SRP II fractions of above-mentioned step and naming them as muGnRH I and muGnRH II respectively.

In still another embodiment of the present invention, wherein fraction SG II increase gonadotropin release by about 20 times.

In still another embodiment of the present invention, wherein fraction SG II increase gonadotropin release by about 20 times.

In still another embodiment of the present invention, wherein fraction MQ I increase gonadotropin release by about 10 times.

In still another embodiment of the present invention, wherein fraction MQ II increase gonadotropin release by about 40 times.

In still another embodiment of the present invention, wherein fraction MS II increase gonadotropin release by about 45 times.

In still another embodiment of the present invention, wherein calcium increase gonadotropin releasing activity of muGnRH I and II.

A method of inducing breeding in fishes using the said novel gonadotropin releasing hormones said method comprising steps of exposing fishes to the said Gonadotropin-releasing hormones to help release gonadotropin, and inducing breeding in fishes using said gonadotropin.

BRIEF DESCRIPTION OF THE ACCOMPANYING DRAWINGS

FIG. 1 shows comparison of primary amino acid sequences of naturally occurring vertebrates and protochordate GnRHs. Underlined amino acids represent differences in forms compared to mammalian GnRH.

FIG. 2 shows hairpin loop of GnRH.

FIG. 3 shows test of murrel GnRH activity in different fractions obtained through acetone fraction. After preparation of three different fractions, 100 micrograms protein was added in vitro pituitary cell culture and release of GtH was measured by RIA.

FIG. 4 shows elution profile of mammalian GnRH through Sephadex G-25 column. AC II fraction was dissolved in 1 N acetic acid and eluted through Sephadex G-25 column (58×1.5 cm) at a flow rate of 24 ml/hr.

FIG. 5a shows elution profile of murrel Sephadex G-25 P-II through FPLC Mono Q column. SG II fraction was dissolved in buffer A-20 mM Tris (pH 8.0) and was injected into the FPLC anion exchange column (Mono Q). At first the column was washed with buffer A and then eluted with buffer B-20 mM Tris (pH 8.0) with 1M NaCl.

FIG. 5b shows elution profile of murrel Mono Q unbound peak (MQ I) through FPLC Mono S column. MQ I was dissolved in buffer A-50 mM ammonium acetate (pH 4.8) and was injected into the FPLC cation exchange column (Mono S). at first the column was washed with buffer A and then eluted with buffer B-50 mM Ammonium acetate(pH 4.8) with 0.5M NaCl.

FIG. 6 shows elution profile of Mono QP-II (a) and Mono SP-II (b) through FPLC Pep-RPC column. GnRH enriched fraction (Mono QP-II) and (Mono SP-II) was dissolved individually in solvent A-0.1% TFA in water and was injected individually into the FPLC peptide reverse phase chromatography (Pep-RPC). Firstly the column was washed with solvent A and then eluted with solvent B-0.1% TFA in acetonitrile.

FIG. 7 shows amino acid sequences of muGnRH I, and muGnRH II.

PURIFICATION OF MURREL GnRH (i) Extraction and Solvent Fractionation:

The hypothalami were homogenized using 1 N acetic acid containing 1 mM PMSF in a Potter-Elvehjem homogenizer under ice. To avoid frothing, homogenization was done very cautiously and slowly. The pH of the crude homogenate was maintained at pH 3.2. The extracted material was filtered through double-fold cheesecloth to remove fat and cell debris.

It was then lyophilized and stored at −80° C. until further use. The dried extract was reconstituted in 0.1 N acetic acid and equal volume of chilled acetone was added and kept at −20° C. for 15 min.

A thick precipitate (AC I) appears at the bottom of the suspension while a clear supernatant is decanted off and to it double the volume of chilled acetone was added and kept at −20° C. for 30 min following which another thin precipitate layer (AC II) appeared. Once again, the clear supernatant was decanted and double the volume of chilled acetone was added to it and kept at −20° C. for 14 h.

This resulted in the appearance of another thin precipitate layer (AC III) and further addition of chilled acetone to the clear supernatant did not result in the formation of any precipitate even after keeping it for 3 days at −20° C. These three acetone fractions were extracted with petroleum ether (40–60° C.) to remove acetone, lipids and other hydrophobic substances.

The final precipitates were centrifuged at 8,000 g for 15 min at 4° C. and the residues were stored at −80° C. until further use. GnRH enriched fraction was identified as AC II on the basis of GTH release from pituitary cell culture in vitro (FIG. 3).

Molecular Exclusion Chromatography:

GnRH was further purified by subjecting AC II to molecular exclusion chromatography on a Sephadex G 25 column. Elution of the column with 0.05 M PBS resulted in two distinct peaks, SG I and SG II (FIG. 4). Mammalian GnRH was consequently run to identify the pattern on the column. On the basis of GTH release from pituitary cell incubation in vitro, GnRH was found to be located in SG II. As shown in table 1 below.

TABLE 1

Biological activities of Sephadex G-25 eluted fractions in terms of GtH release from murrel pituitary cell incubations

| System* | GtH released (ng/6 × $10^4$ cells) |
|---|---|
| Control (C) | 2.8 ± 0.18 |
| C + SG I | 9.3 ± 0.93 |
| C + SG II | 37.9 ± 2.18 |

(ii) Ion Exchange Chromatography:

This was further purified by FPLC Mono Q (anionic) and Mono S (cationic) ion-exchange chromatography. The pooled, dialysed and lyophilised active peak of the molecular exclusion chromatographic step (SG II) was loaded on a Mono Q column; washing the Mono Q column with 20 mM Tris (pH 8.0) gave rise to a unbound peak (MQ I) while on gradient elution with NaCl (1.0 M) containing 20 mM Tris (pH 8.0), three bound peaks (MQ II, MQ III and MQ IV) were obtained (FIG. 5a).

Assay of GnRH activity on the basis of GTH release from in vitro pituitary cell culture identified the bound MQ II to possess the maximum GnRH activity while MQ III and MQ IV showed negligible activity (As shown below in Table 2a).

TABLE 2a

Biological activities of FPLC Mono Q and Mono S eluted fractions in terms of GtH release from murrel pituitary cell incubations

| System[a] | GtH released (ng/6 × $10^4$ cells) |
|---|---|
| Control (C) | 2.5 ± 0.17 |
| C + MQ I | 21.6 ± 0.98 |
| C + MQ II | 77.5 ± 2.92 |
| C + MQ III | 2.7 ± 0.29 |
| C + MQ IV | 2.3 ± 0.34 |

TABLE 2a-continued

Biological activities of FPLC Mono Q and Mono S eluted fractions in terms of GtH release from murrel pituitary cell incubations

| System[a] | GtH released (ng/6 × $10^4$ cells) |
|---|---|

[a]2 μg protein from each peak was added to the incubation systems. Values are mean ± SEM of four experiments Surprisingly the unbound peak of the Mono Q elution (MQ I) also showed significant amounts of GnRH activity thus indicating the presence of a cationic form of GnRH.

MQ I was therefore loaded onto a Mono S (cationic) column; washing the column with 50 mM ammonium acetate (pH 4.8) gave rise to a single unbound peak (MS I) while on subsequent gradient elution with 0.5 M NaCl, three bound peaks (MS II, MS III and MS IV) were obtained (FIG. 5b). Assay of GnRH activity in all the four peaks identified MS II to be highly enriched in GnRH (As shown below in table 2b).

TABLE 2b

| System[a] | GtH released (ng/6 × $10^4$ cells) |
|---|---|
| Control (C) | 2.4 ± 0.16 |
| C + MS I | 3.4 ± 0.23 |
| C + MS II | 83.1 ± 3.46 |
| C + MS III | 3.0 ± 0.18 |
| C + MS IV | 2.6 ± 0.09 |

[a]2 μg protein from each peak was added to the incubation systems. Values are mean ± SEM of four experiments (iii) Reverse Phase Chromatography:

We now had two forms of GnRH in hand—one anionic form (MQ II) and the other cationic form (MS II). Both were further purified through Pep-RPC column chromatography. After loading the column with either MQ II or MS n, in both the cases, the unbound proteins were eluted with 0.1% trifluoroacetic acid in water while the bound material was eluted with 0.1% trifluoroacetic acid in acetonitrile gradient. MQ II resolved into one unbound peak (QRP I) and two bound peaks (QRP H and QRP HI) (FIG. 6a); MS H gave rise to one unbound (SRP I) and two bound (SRP II and SRP ID) peaks (FIG. 6b). GnRH was found to be located in QRP H and SRP H (FIG. 6 insets) and were termed muGnRH I (anionic) and muGnRH H (cationic).

(iv) Functional Activity of the Purified GnRHs

Both muGnRH I and muGnRH II are highly active in releasing GTH from murrel pituitary cells, muGnRH II being slightly more active. Moreover, these two GnRHs act almost equally in different species of carp indicating no species barrier (As shown below in Table 3).

TABLE 3

A comparison of gonadotropin release from the pituitaries of different carps in response to murrel GnRH I and II

| Carp species | Incubations (2 μg GnRH fractions) | GtH II released (ng/6 × $10^4$ cells) |
|---|---|---|
| Catla catla | Control (C) | 2.6 ± 0.32 |
| | C + mGnRH I | 74.5 ± 2.32 |
| | C + mGnRH II | 82.6 ± 3.02* |
| Cirrhinus mrigala | Control (C) | 2.1 ± 0.24 |
| | C + mGnRH I | 72.0 ± 2.13 |
| | C + mGnRH II | 80.1 ± 2.61* |

TABLE 3-continued

A comparison of gonadotropin release from the pituitaries of different carps in response to murrel GnRH I and II

| Carp species | Incubations (2 μg GnRH fractions) | GtH II released (ng/6 × $10^4$ cells) |
|---|---|---|
| Cyprinus carpio | Control (C) | 2.8 ± 0.22 |
| | C + mGnRH I | 73.8 ± 2.51 |
| | C + mGnRH II | 81.7 ± 3.12* |

*p < 0.01 as compared to control

Surprisingly, when added in combination, muGnRH I and II exhibit highly significant increase in GTH release as a result of combination (As shown below in Table 4).

TABLE 4

| Incubations (2 μg GnRH fractions) | GtH released (ng/6 × $10^4$ cells) |
|---|---|
| Control (C) | 2.6 ± 0.18 |
| C + mGnRH I | 73.3 ± 2.2* |
| C + mGnRH II | 79.2 ± 3.12* |
| C + mGnRH 1 + mGnRH II | 115.0 ± 3.23** |
| mammalian GnRH | 49.9 ± 2.02 |
| salmon GnRH (synthetic) | 56.2 ± 2.15 |
| GnRH superactive analogue (des-Gly[10],[D-Ala[a]]-LHRH) | 68.0 ± 2.32 |

Values are mean ± SEM of five experiments.
*p < 0.0 when compared with mammalian or salmon GnRHs
**p < 0.01 as compared with GnRH superactive analogue In fact, whether alone or in combination, muGnRHs had significantly greater activity as compared to mammalian GnRH, salmon GnRH or the GnRH superactive analogue.

In an embodiment of the present invention addition of calcium to GnRH I and II enhance the gonadotropin releasing activity of GnRH I and II.

Both these synthesized GnRHs showed much greater activity in the laboratory and field experiments as compared to salmon GnRH, its analogues and other superactive analogues and commercial product "Ovaprim". Amino acid sequence of these two decapeptides (murrel GnRH I and II) could not be given here as we have applied for patent. This Indian Product (murrel GnRH I plus II) therefore has great promise for national and international market.

The above mentioned results placed Indian murrel GnRHs (I plus II) as a highly promising global competitor since Salmon GnRH analogue (Ovaprim) prepared by Syndel Laboratory, Canada is dominating the market and extensively sold all over the world to breed culturable fish.

Both the murrel GnRHs (GnRH I and II) are novel, no naturally occurring GnRH discovered till date has such sequences (FIG. 7). The activity of the synthetic GnRHs has been examined in the laboratory (pituitary cell culture) and field to breed carps.

A method of inducing breeding in fishes using the said novel gonadotropin releasing hormones said method comprising steps of exposing fishes to the said Gonadotropin-releasing hormones to help release gonadotropin, and inducing breeding in fishes using said gonadotropin.

What is claimed is:

1. An isolated gonadotropin releasing hormone selected from the group consisting of muGnRH I (SEQ ID NO:1) and muGnRH II (SEQ ID NO:2).

2. The hormone as claimed in claim 1, wherein said hormone is obtained from Indian Murrel brain.

3. The hormone muGnRH II (SEQ ID NO:2) as claimed in claim 1 which is more active than gonadotropin-releasing hormone muGnRH I (SEQ ID NO:1).

4. The hormone muGnRH I (SEQ ID NO:1) as claimed in claim 1 which increases gonadotropin release by about 30 times as compared to the level of gonadotropin release in the absence of muGnRH I (SEQ ID NO:1) and muGnRH II (SEQ ID NO:2).

5. The hormone muGnRH II (SEQ ID NO:2) as claimed in claim 1 which increases gonadotropin release by about 35 times as compared to the level of gonadotropin release in the absence of muGnRH I (SEQ ID NO:1) and muGnRH II (SEQ ID NO:2).

6. A composition comprising isolated gonadotropin releasing hormones muGnRH I (SEQ ID NO:1) and muGnRH II (SEQ ID NO:2) which exhibit synergy in induced breeding of fish.

7. A composition comprising the muGnRH I (SEQ ID NO: 1) and muGnRH II (SEQ ID NO:2) as claimed in claim 1 in a ratio of about 1:1 which increases gonadotropin release by about 50 times as compared to the level of gonadotropin release in the absence of muGnRH I (SEQ ID NO: 1) and muGnRH II (SEQ ID NO:2).

8. The hormone muGnRH I (SEQ ID NO:1) as claimed in claim 1, wherein said hormone shows no species barrier in induced breeding of fish and wherein there is an increase in gonadotropin release ranging between 20–50 times as compared to the level of gonadotropin release in the absence of muGnRH I (SEQ ID NO:1) and muGnRH II (SEQ ID NO:2).

9. The hormone muGnRH II (SEQ ID NO:2) as claimed in claim 1, wherein said hormone shows no species barrier in induced breeding of fish and wherein there is an increase in gonadotropin release ranging between 20–50 times as compared to the level of gonadotropin release in the absence of muGnRH I (SEQ ID NO:1) and muGnRH II (SEQ ID NO:2).

10. The hormone muGnRH I (SEQ ID NO:1) as claimed in claim 1, wherein said hormone is more active than other GnRHs selected from the group consisting of mammalian GnRH, Salmon GnRH, GnRH superactive analogues, and commercially available GnRH Ovaprim or a combination thereof.

11. The hormone muGnRH II (SEQ ID NO:2) as claimed in claim 1, wherein said hormone is more active than other GnRHs selected from the group consisting of mammalian GnRH, Salmon GnRH, GnRH superactive analogues, and commercially available GnRH Ovaprim or a combination thereof.

* * * * *

UNITED STATES PATENT AND TRADEMARK OFFICE
CERTIFICATE OF CORRECTION

PATENT NO.        : 6,977,242 B2
APPLICATION NO. : 10/354433
DATED             : December 20, 2005
INVENTOR(S)       : Abhijit Chatterjee et al.

It is certified that error appears in the above-identified patent and that said Letters Patent is hereby corrected as shown below:

On title page, item 75, "Hattacharya" should read -- Bhattacharya --.

Signed and Sealed this

First Day of August, 2006

JON W. DUDAS
*Director of the United States Patent and Trademark Office*

SEQUENCE LISTING

<160> NUMBER OF SEQ ID NOS: 2

<210> SEQ ID NO 1
<211> LENGTH: 10
<212> TYPE: PRT
<213> ORGANISM: channa punctatus

<400> SEQUENCE: 1

Gln His Trp Ser Ala Trp Arg Leu Pro Gly
1               5                   10

<210> SEQ ID NO 2
<211> LENGTH: 10
<212> TYPE: PRT
<213> ORGANISM: channa punctatus

<400> SEQUENCE: 2

Gln His Trp Ser Trp Gly Ile Leu Pro Gly
1               5                   10